United States Patent [19]

Lewis et al.

[11] 4,228,306

[45] * Oct. 14, 1980

[54] PHENYLENE SUBSTITUTED POLYMERIC DIALKYL PEROXIDES

[75] Inventors: Roger N. Lewis, Martinez; Lawrence A. Bock, Redwood City, both of Calif.

[73] Assignee: Argus Chemical Corporation, Brooklyn, N.Y.

[*] Notice: The portion of the term of this patent subsequent to Mar. 27, 1996, has been disclaimed.

[21] Appl. No.: 956,712

[22] Filed: Nov. 1, 1978

Related U.S. Application Data

[62] Division of Ser. No. 819,318, Jul. 27, 1977, Pat. No. 4,146,583.

[51] Int. Cl.$^3$ ............... C07C 179/035; C07C 179/047
[52] U.S. Cl. .................................................. 568/563
[58] Field of Search ................................. 568/563, 561

[56] References Cited

U.S. PATENT DOCUMENTS

| | | | |
|---|---|---|---|
| 3,402,205 | 9/1968 | Gregory | 568/563 |
| 3,419,577 | 12/1968 | Bieber et al. | 568/561 |
| 3,764,628 | 10/1973 | Gregorian | 568/563 |
| 3,775,465 | 11/1973 | Sacrinie et al. | 568/563 |
| 3,787,504 | 1/1974 | Peri | 568/563 |

FOREIGN PATENT DOCUMENTS

| | | | |
|---|---|---|---|
| 767709 | 9/1967 | Canada | 568/561 |
| 572453 | 10/1977 | U.S.S.R. | 568/561 |

Primary Examiner—Werren B. Lone
Attorney, Agent, or Firm—Townsend and Townsend

[57] ABSTRACT

Cyclic and acyclic phenylene substituted dialkyl peroxides most of which are in an acyclic polymeric form.

8 Claims, No Drawings

PHENYLENE SUBSTITUTED POLYMERIC DIALKYL PEROXIDES

This is a division of application Ser. No. 819,318, filed July 27, 1977, now U.S. Pat. No. 4,146,583.

This invention relates to novel organic peroxides and their method of preparation. More particularly, it relates to cyclic and acyclic phenylene substituted dialkly peroxides most of which are in an acyclic polymeric form.

U.S. Pat. No. 3,419,577 discloses a group of aliphatic acyclic and cyclic organic peroxides having internal peroxide groups including organic peroxide polymers formed by etherifying an aliphatic diol with an aliphatic dihydroperoxide. The present compositions include a different group of polymeric and cyclic structures with the further difference that the instant peroxides contain phenylene substitution.

More particularly, the present invention provides organic peroxides selected from the group consisting of:

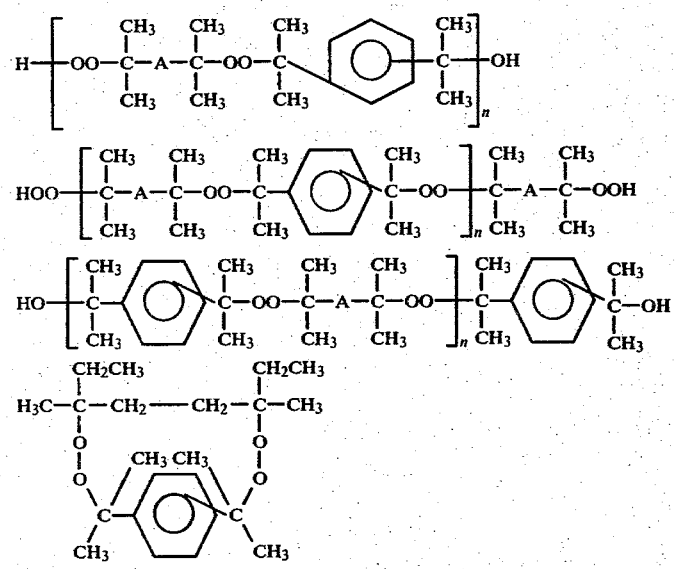

wherein

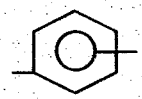

represents a 1,4 or 1,3 ring attachment, A represents —CH$_2$—CH$_2$— or —C≡C—, and n is a positive integer from 1–5.

Preferred peroxides are obtained when in Formula I the ring attachments are in the 1,4 positions, A is —CH$_2$—CH$_2$— and n is 2–4. Other preferred structures in relation to Formula I are when the ring attachments are in the 1,3 positions and A is —CH$_2$—CH$_2$— and n is 1–2. Another group of preferred structures relative to Formula I is when the ring attachments are in the 1,4 positions, A is —C≡C— and n is 2–4.

With respect to Formula II, preferred peroxides are obtained when the ring attachments are in the 1,4 positions, A is —CH$_2$—CH$_2$— and n is 1–3. Within this latter class, a preferred structure in relation to Formula II is when the predominant species has the formula in which n is 2.

With respect to Formula III, preferred peroxides are obtained when the ring attachments are in the 1,4 positions, A is —CH$_2$—CH$_2$— and n is 1–3. Within this latter class, a preferred structures relative to Formula III is when the predominant species has the formula in which n is 2.

With respect to Formula IV, preferred compositions have the ring attachments in the 1,4 positions.

In the preferred embodiment the organic peroxides of this invention are prepared by an etherification reaction under conditions similar to that described in U.S. Pat. No. 3,419,577. In general, the reaction provides a mixture of compounds. If desired, the mixture can be isolated into individual components. However, it is generally unnecessary to make such a separation and the mixtures may be used as such for most applications.

More particularly, the present compounds are preferably formed by etherifying at least one diol selected from 1,4-bis(hydroxyisopropyl)benzene of the formula:

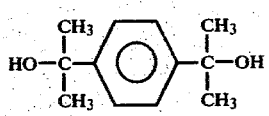

and 1,3-bis(hydroxyisopropyl)benzene of the formula:

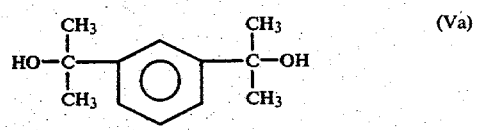

with at least one dihydroperoxide selected from 2,5-dimethyl-2,5-dihydroperoxyhexane of the formula:

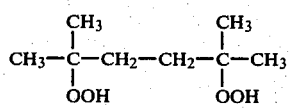

2,5-dimethyl-2,5-dihyroperoxyhexyne-3 of the formula:

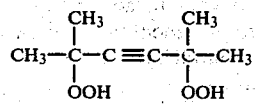

and 3,6-dimethyl-3,6-dihydroperoxyoctane of the formula:

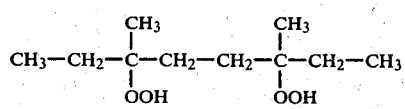

The polymeric peroxides of Formulas I and IV are obtained by reacting the selected diol and the selected dihydroperoxide in equimolar quantities. The polymeric peroxide of Formulas II and III are obtained by reacting the diol and the dihydroperoxide in a 1:2 or 2:1 molar ratio. The peroxides of Formula II are obtained by reacting two moles of dihydroperoxide with one mole of diol. Conversely, Formula III is obtained by reacting two moles of diol with one mole of dihydroperoxide.

Although the foregoing method of preparing the instant new compositions is preferred, it is also possible to prepare the same peroxides with alternative starting materials. For example, the following reactions will also result in the novel peroxides of Formula I of this invention.

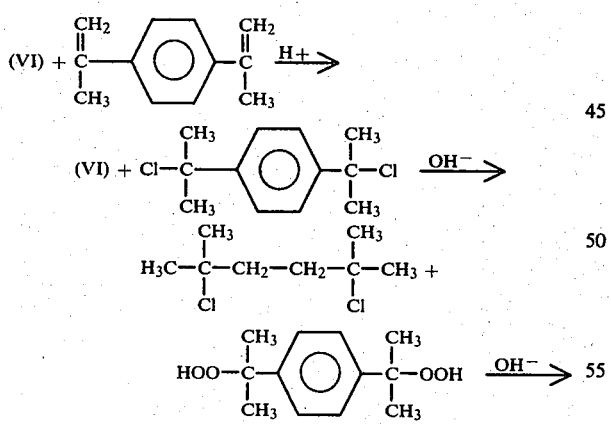

Products of the present invention have utility as crosslinking or vulcanizing agents of polyolefins or various elastomers. They can be also used as high temperature catalysts for the curing of unsaturated polyester resins with crosslinkable monomers.

The following experimental work illustrates preparation and utility of the present compositions. In the work reported below comparisons have been made against 1,3-bis(t-butyl peroxyisopropyl)benzene because it is a commercial peroxide with a nonpolymeric structure somewhat similar to the repeating unit from Formula I, that is

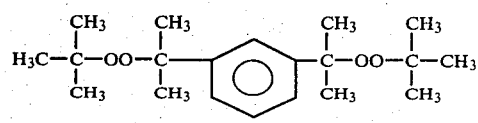

In addition, 2,5-dimethyl-2,5-di(t-butyl peroxy)hexyne-3 was used for comparison because it is a commercial peroxide used to crosslink high density polyethylene (HDPE).

EXAMPLE 1—REACTION BETWEEN V AND VI

A solution of 7.76 g (0.04 mole) of 1,4-bis(hydroxyisopropyl) benzene (V) was prepared in 45 ml of warm glacial acetic acid. This solution was then added to 7.24 g of 98.27% (0.04 mole) 2,5-dimethyl-2,5-dihydroperoxy hexane (VI) dissolved in 45 ml glacial acetic acid in a 125 ml round bottom flask equipped with a mechanical stirrer and thermometer. The mixture was cooled to 15° C. Then 0.1 g of 70% $HClO_4$ in 10 ml glacial acetic acid was added to several portions over about a one-minute period. Within one minute after completion of the acid addition, the solution began to turn cloudy, and a solid began to precipitate. The suspension was stirred for an additional 2 hours at 15° C. and then dumped into 200 ml of ice water. The aqueous layer was removed by suction, additional water and $NaHCO_3$ added to bring the pH to about 6, and the solid product was finally collected by filtration and dried in a vacuum oven. Yield: 12.3 g (91.5%). Characterization of this product is shown in Table 1 as entry 1(b). The other dialkyl peroxides shown in Table 1 were prepared by essentially the same method by substituting the necessary amounts of the other two alkyl dihydroperoxides (VII and VIII) or 1,3-bis(hydroxyisopropyl) benzene (Va).

Experimental

1. Press Molding of Low Density Polyethylene (LDPE)

The desired amount of peroxide was dryblended into 30.0 g of powdered LDPE resin[1]) by stirring for 5 minutes with a spatula. Aluminum foil was used to cover the platens. Platen temperatures on the press were checked with a surface pyrometer and were 320±5° F. (160° C.) Cure time was 30 minutes. It started when the ram gauge read 1,000 PSIG. Final pressure was between 4,000–8,000 PSIG. At the end of the cure time the pressure was released immediately. Trays were removed from the molds and cooled quickly in a water bath. The aluminum foil was removed from the tray by immersing it in approximately 18–20% HCl solution.
[1])Rexene XOA 2(206) - F2.

To determine the %wt gel, an approximately 0.3 g sample was cut into 6–7 pieces and placed inside a stainless steel screen pouch. These pouches were extracted in 2 liters of boiling xylene containing 10 g of Plastonox 2246 anti-oxidant for 16 hours and then dried in an oven at 170° C. for 4 hours. Results are shown in Table 2.

The %wt gel was calculated by the following formula:

$$\% \text{ wt gel} = \frac{W_1 - (W_2 - W_3) - W_{B1} \times 100}{W_1}$$

Where:
$W_1$ = wt. of sample, g.
$W_2$ = wt. of sample + pouch, g.
$W_3$ = wt. of sample + pouch after extraction, g.
$W_{B1}$ = blank value for resin without peroxide.

2. Crosslinking or Vulcanizing Various Resins in a Torque Rheometer

A Brabender Plasticorder at a rotor speed of 30 RPM was used for these tests. For polyolefins, the Roller-6 blades were used; for the elastomers, the Cam blades were used. The desired weight of a particular resin was added to the Plasticorder maintained at the desired temperature. At either 12 or 16 minutes, the correct weight of peroxide on a carrier or in n-hexane solution was added directly to the mixing head. Net torque is equal to the maximum torque minus the torque at peroxide addition. Time to reach maximum torque is the time at maximum torque minus the time of peroxide addition. If an additive was used, it was added to the mixing head after 7 minutes. The following amounts of various resins were used in these tests:

| Resin | Wt, g | Table |
|---|---|---|
| 1. Union Carbide DYNH low density polyethylene (LDPE) pellets | 35 or 40 | 3 |
| 2. USI Microthene "F" LDPE powder (peroxide carrier) | 5 | 3 |
| 3. Phillips Marlex BMN5565 high density polyethylene (HDPE) pellets | 40 | 4 |
| 4. Copolymer Epsyn 4506 ethylene propylene diene rubber (EPDM) | 40 | 4 |
| 5. Dow 3614 chlorinated polyethylene (CPE) powder | 40 | 4 |

Footnote:
In Table 3, when a carrier other than Burgess clay is used with the polymeric dialkyl peroxides, there is an induction period after the peroxide is added when no crosslinking occurs. The reason for this phenomenon is unknown.

TABLE 1

Dialkyl Peroxides from α,α'-Dihydroxy Diisopropyl Benzene and Various Alkyl Dihydroperoxides Using $HClO_4$ as an Acid Catalyst

| Reactants | | Mole Ratio | Reaction Time Hrs. | Temp., °C. | % Yield of Product | M.W. | m.p., °C. | Active Oxygen Analysis Total A.O. | —OOH A.O. | Chromatographic Analysis (Area %)[1] Polymeric Peroxides | Starting Material |
|---|---|---|---|---|---|---|---|---|---|---|---|
| 1. V + VI | (a) | 1:1 | 2 | 15 | 90.2 | 1097 avg. | 92-102 | 9.15 avg. | 1.09 | 96 | 4 |
| | (b) | 1:1 | 2 | 15 | 91.5 | 1075 | 86-96 | 9.86 avg. | 1.37 avg. | 94 | 6 |
| | (c) | 1:2 | 2 | 15 | 70.8 | 763 | 85-91 | 10.75 avg. | 3.24 avg. | 96 | 4 |
| | (d) | 2:1 | 2 | 15 | 78.8 | 748 | 80-86 | 7.76 avg. | 0.25 avg. | 96 | 4 |
| 2. Va + VI | (a) | 1:1 | 2.5 | 15-25 | ND[2] | 475 | liquid | 6.46 avg. | 1.18 | 95 | 5 |
| | (b) | 1:1 | 5.5 | 15-20 | ND | 525 | same | 6.64 | 1.16 | | |
| 3. V + VII | | 1:1 | 93 | 15-20 | ND | 849 | 73-75 | 7.05[3] | 0.57 | 93 | 7 |
| 4. V + VIII | | 1:1 | 2 | 15-20 | ND | 305 | liquid | 7.92 avg. | 0.41 | 74 | 26[4] |

[1] Products from items 1-3 were done by GPC; product from item 4 was done by LC.
[2] Not determined
[3] —C≡C— group interferes with Total A.O. analysis.
[4] Approximately 40% is the aromatic diol and 60% is the alkyl dihydroperoxide.

TABLE 2

Crosslinking LDPE by Press Molding at 320° F. (160° C.) for 30 Minutes with various Peroxides

| | Peroxide | M.W. | phr[1] | % wt Gel |
|---|---|---|---|---|
| 1. | Blank | — | — | 0.5 |
| 2. | BTBIB[2] | — | 2.5 | 91.1 |
| 3. | V + VI[3] | 1097 | 2.5 | 56.9, 58.0 |
| 4. | Va + VI[3] | 525 | 2.5 | 35.8 |

[1] On a 100% purity basis for BTBIB and on an "as-is" basis for other peroxides.
[2] 1,3-Bis(t-butyl peroxyisopropyl) benzene.
[3] Peroxide obtained from reaction of equimolar amounts of each indicated reactant.

TABLE 3

Crosslinking LDPE in the Brabender Plasticorder with Various Peroxides

| | Peroxide[1] | M.W. | phr[2] | Peroxide Carrier | Head Temp., °C. | Induction Period After Adding Peroxide, Min. | Time to Complete Crosslinking, Min. | Total Time to Maximum Torque, Min. | Net Torque, mg. |
|---|---|---|---|---|---|---|---|---|---|
| 1. | BTBIB[3] | — | 2.5 | LDPE Powder | 160 | — | — | 5.2, 6.0 | 1170, 1150 |
| 2. | V + VI | (a) 1097 avg. | 2.5 | same | 160 | 12.5 | 13.5 | 26.0 | 1320 |
| | | | 2 | same | 170 | 3.0, 4.0 | 9.5, 9.0 | 12.5, 13.0 | 1220, 1290 |
| | | (b) 1075 | 2.5 | Burgess clay | 160 | — | — | 15.5 | 1360 |
| | | | 2 | same | 170 | — | — | 4.5, 5.2 | 1200, 1230 |
| 3. | V + 2 VI | 763 | 2 | LDPE Powder | 170 | 2.0 | 10.0 | 12.0 | 1010 |
| 4. | 2 V + VI | 748 | 2 | same | 170 | 1.5 | 11.5 | 13.0 | 1160 |
| 5. | Va + VI | 475 | 2 | n-hexane | 170 | 8.0 | 6.0 | 14.0 | 700 |
| 6. | V + VII | 849 | 2 | Burgess clay | 170 | — | — | 30.0 | 1000 |

[1] Peroxide used was that obtained from reaction of reactants in mole ratios indicated.
[2] On a 100% purity basis for BTBIB and on an "as-is" basis for other peroxides.
[3] 1,3-Bis(t-butyl peroxyisopropyl) benzene

TABLE 4

Crosslinking Various Polymers in the Brabender Plasticorder with Various Peroxides on Burgess Clay

| | Peroxide[1] | M.W. | phr[2] | Polymer | Additive, phr | Head Temp., °C. | Time to Max. Torque, Min. | Net Torque mg. |
|---|---|---|---|---|---|---|---|---|
| 1. | BTBIB[3] | — | 7.5 | EPDM | — | 160 | 2.0 | 460 |
| 2. | V + VI | 1075 | 7.5 | EPDM | — | 160 | 3.2 | 520 |
| 3. | BTBIB | — | 7.5 | CPE | 2 Mark WS 3 Mark 224 | 160 | 3.0 | 260 |
| 4. | V + VI | 1075 | 7.5 | CPE | same as above | 160 | 5.0 | 420 |
| 5. | DMDTBH-3[4] | — | 0.5[5] | HDPE | — | 190 | 8.8 | 3480 |
| 6. | V + VII | 849 | 1.25 | HDPE | — | 190 | 7.3 | 2340 |

[1]Peroxide used was that obtained from reaction of reactants in mole ratios indicates.
[2]On a 40% active basis
[3]1,3-Bis(t-butyl peroxyisopropyl) benzene
[4]2,5-Dimethyl-2,5-di-t-butyl peroxy hexyne-3
[5]On a 100% purity basis, diluted in n-hexane

TABLE 5

Hot-Block Gel Tests with Various Peroxides in Hatco GR-14010 Unsaturated Polyester Resin at 275° F.
Catalyst Concentration: 1.0% wt (100% purity basis)

| | Peroxide[1] | M.W. | Gel Time, Min. | Exotherm Time, Min. | Peak Temp., °F. |
|---|---|---|---|---|---|
| 1. | BTBIB[2] | — | 2.12 | 2.68 | 367.5 |
| | | | 2.06 | 2.56 | 370 |
| 2. | V + VI | 1097 | 2.68 | 3.11 | 381 |
| | | | 2.50 | 2.93 | 368 |
| 3. | Va + VI | 500 | 2.21 | 2.66 | 373 |
| | | | 2.22 | 2.72 | 378 |
| 4. | V + VII | 849 | 2.67 | 3.22 | 385 |
| | | | 2.59 | 3.18 | 386 |
| 5. | V + VIII | 305 | 2.45 | 2.92 | 375 |
| | | | 2.43 | 2.92 | 377.5 |

[1]Peroxide used was that obtained from reaction of reactants in mole ratios indicated.
[2]1,3-Bis(t-butyl peroxyisopropyl) benzene

We claim:

1. A method for making a phenylene substituted dialkyl peroxide comprising: etherifying a diol selected from 1,4-bis(hydroxyisopropyl)benzene and 1,3-bis(hydroxyisopropyl)benzene with a dihydroperoxide selected from 2,5-dimethyl-2,5-dihydroperoxyhexane, 2,5-dimethyl-2,5-dihydroperoxyhexyne-3, and 3,6-dimethyl-3,6-dihydroperoxyoctane, said diol and dihydroperoxide being present in co-reactive amounts and under conditions which permit etherification therebetween, and recovering the organic peroxide reaction product.

2. A method for making a phenylene substituted dialkyl peroxide in accordance with claim 1 in which the diol and the dihydroperoxide are reacted in equimolar quantities.

3. A method for making a phenylene substituted dialkyl perioxide in accordance with claim 1 in which two moles of the diol are reacted with one mole of dihydroperoxide.

4. A method for making a phenylene substituted dialkyl peroxide in accordance with claim 1 in which two moles of dihydroperoxide are reacted with one mole of diol.

5. The product obtained by the method of claim 1.
6. The product obtained by the method of claim 2.
7. The product obtained by the method of claim 3.
8. The product obtained by the method of claim 4.

* * * * *